United States Patent [19]

Hayashi et al.

[11] Patent Number: 5,225,321
[45] Date of Patent: Jul. 6, 1993

[54] MEASURING APPARATUS USING ENZYME ELECTRODES AND THE METHOD THEREOF

[75] Inventors: Ryuzo Hayashi, Higashiosaka; Akio Kariyone, Kyoto; Yoshio Hashizume, Nishinomiya, all of Japan

[73] Assignee: Kanzaki Paper Mfg., Co., Ltd., Tokyo, Japan

[21] Appl. No.: 727,341

[22] Filed: Jul. 8, 1991

Related U.S. Application Data

[63] Continuation of Ser. No. 242,415, Sep. 8, 1988, abandoned.

[30] Foreign Application Priority Data

Sep. 11, 1987 [JP] Japan .................. 62-228730

[51] Int. Cl.$^5$ .................. G01N 27/327; G01N 33/573; G01N 33/66
[52] U.S. Cl. .................. 435/4; 435/280; 435/291; 204/403; 204/153.12; 422/82.03
[58] Field of Search .................. 435/4, 291, 288, 817; 204/403, 1 T; 422/68.1, 82.02, 82.03

[56] References Cited

U.S. PATENT DOCUMENTS

| | | | |
|---|---|---|---|
| 3,707,455 | 7/1968 | Derr et al. | 204/1 T |
| 4,169,765 | 10/1979 | Keyes | 435/291 |
| 4,195,127 | 3/1980 | Hartdegen | 435/174 |
| 4,467,811 | 8/1984 | Clark, Jr. | 128/635 |
| 4,525,265 | 6/1985 | Abe et al. | 204/403 |
| 4,552,840 | 11/1985 | Riffer | 435/14 |
| 4,680,270 | 7/1987 | Mitsumaki et al. | 436/52 |

FOREIGN PATENT DOCUMENTS

| | | |
|---|---|---|
| 0216946 | 12/1983 | Japan . |
| 216947 | 12/1983 | Japan . |
| 5172 | 1/1987 | Japan . |
| 24142 | 2/1987 | Japan . |
| 2063479 | 6/1981 | United Kingdom . |

OTHER PUBLICATIONS

Yao et al., "Analytical Biochemistry" 149, 387-391 (1985).
Patent Abstracts of Japan, 10 (271) (P-497) [2327], Sep. 16, 1986.
Pfeiffer et al., "Biochimie", 62, 587-593 (1980).
C. Bertrand et al., Analytica Chimica Acta, vol. 126, pp. 23-34 (1981).
F. Scheller et al., Analytica Chimica Acta, vol. 152, pp. 265-269 (1983).
M. Massoom et al., Analytica Chimica Acta, vol. 171, pp. 185-194, (1985).

*Primary Examiner*—James C. Housel
*Assistant Examiner*—David Redding
*Attorney, Agent, or Firm*—Wenderoth, Lind & Ponack

[57] ABSTRACT

In the case of measuring concentration of, for example, glucose as a first substance to be measured, and that of sucrose as a second substance to be measured, using a measuring apparatus, the apparatus is provided with a first enzyme electrode, a dilution pipeline situated at the downstream of the electrode and for diluting the substances, and a second enzyme electrode situated at the downstream of the dilution pipeline. A sample, which contains the first and second substances, is poured intermittently into a constant flow of a buffer solution. The first enzyme electrode detects the first substance. The second enzyme electrode, which comprises an immobilized enzyme catalizing the conversion of the second substance in to the first substance, detects the first substance, which is originally contained in the sample as well as is formed on the second enzyme electrode. The concentration of the second substance in the sample can be determined by calculating about the outputs of the first and second enzyme electrodes.

15 Claims, 15 Drawing Sheets

MEASURING APPARATUS USING ENZYME ELECTRODES AND THE METHOD THEREOF

This application is a continuation of now abandoned application, Ser. No. 07/242,415 filed Sep. 9, 1988.

BACKGROUND OF THE INVENTION

1. Field of the Invention

The present invention concerns a flow type measuring apparatus which has enzyme electrodes, and measures concentrations of two different substances. More specifically, the invention relates to an improvement of the apparatus, having two enzyme electrodes which ultimately detect the same material, and on one enzyme electrode thereof, a first substance to be measured is yielded from a second substance by enzymatic reaction.

2. Description of the Prior Art

In recent years, immobilized enzymes have been broadly applied to the fields of clinical testing, fermenation and analytical chemistry. Especially, immobilized enzyme electrodes are frequently utilized, because of their high selectivity, readiness and easiness of measuring.

Recently, there have been efforts to develop the apparatus measuring two different substances. For instance, apparatus were introduced, which measures simultaneously;

(1) glucose and uric acid (the Japanese Laid-open Patent Publication No. 24142/1987), (2) lactic acid and Pyruvic acid (the Japanese Laid-open Patent Publication No. 5172/1987), (3) glucose and latic acid, or glucose and choline (GB 2063479), and so on. According to these prior arts, however, each enzyme immobilized on the electrode catalyzes the different reaction respectively.

On the contrary, in the case of common reaction, which yields or consumes the electrode active material (for example, ultimately hydrogen peroxide is formed, and the amount of the hydrogen peroxide is measured), the concentration of one substance (e.g. glucose) can be measured by one electrode, but the other electrode detects not only hydrogen peroxide originated from the other substance (e.g. sucrose) but also hydrogen peroxide originated from one substance (glucose). So one substance (glucose) can be measured, but the result of measurement of the other is addition of the values of two substances.

For example, in the case of measuring sucrose concentration in the sample containing both glucose and sucrose using the enzyme electrodes, the result is effected by glucose concentration.

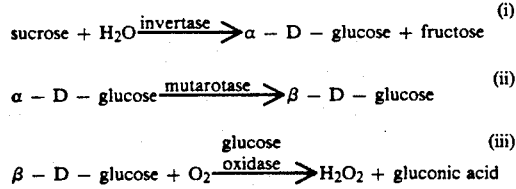

Generally in order to measure sucrose concentration, sucrose is hydrolyzed to fructose and α- D-glucose by invertase (formula (i)). Thereafter α- D - glucose is converted to β- D - glucose by mutarotase (formula (ii)). And hydrogen peroxide, that is electrode active material, is formed as a result of oxidation of β- D-glucose catalyzed by glucose oxidase. This hydrogen peroxide is detected by the enzyme electrode electrochemically (C. Bertrand P. R. Coulet, D. C. Gautheron, Anal. Chim, Acta, 126,23-34(1981). But according to this method, the enzyme electrode measures not only β- D- glucose converted from sucrose by formula (i) and (ii), but also β- D - glucose originally contained in the sample, because β- D - glucose originally contained in the sample yields hydrogen peroxide by the formula (iii), as well as β- D - glucose formed by the formula (i), (ii ) does.

Therefore, in order to measure correct concentration of only sucrose, it is necessary;

to provide the layer containing glucose oxidase and catalase, in which glucose is oxidized by the glucose oxidase and hydrogen peroxide is removed by the catalase enzymatically before measuring sucrose(F. Scheller, R. R enneberg, Anal. Chim. Acta, 152, 265-269(1983)), or to employ enzymatic reaction and electrochemical techinique in order to remove influence of glucose originally contained in the sample (the Japanese Laid-open Patent Publication No. 216947/1983).

But the apparatus employed in the above described method have some drawbacks that it is extremely difficult to immobilize the enzymes to the membrane in preparing the enzyme electrode and that the electrode itself must be so complicated. Furthermore, in order to measure two different substances, that is glucose as well as sucrose, another electrode must be provided and glucose concentration is measured by this electrode.

Recently reported was a flow type measuring apparatus, which comprises a column reactor cycling a sample solution (M. Massoom, A. Townshend, Anal. Chim. Acta, 171, 185-194(1985)). This apparatus, however, is complicated and far greater amount of enzyme is needed to compare with the apparatus having the enzyme electrodes. And it also had a drawback in that it gives a result incorrectly because of choking of the column.

The case of measuring the sample containing both sucrose and glucose is described above, however, when the same electrode active material is formed by the common enzymatic reaction on the two enzyme electrodes, in measuring two different substances simultaneously, for example in measuring maltose and glucose, or ester type cholesterol and free cholesterol, the same kinds of problems are caused.

So the inventors employed a measurement of concentrations of two different substances, for example glucose as the first substance to be measured, and sucrose as the second substance to be measured, using two enzyme electrodes by following method. A flow type measuring apparatus is prepared, which is provided with a first enzyme electrode having immobilized glucose oxidase for measuring glucose, and a second enzyme electrode having immobilized glucose oxidase, mutarotase and invertase for measuring sucrose.

A detected glucose concentration by the first enzyme electrode is calculated, and correct concentration of sucrose only is given by subtracting the result of the calculation from the output current value of the second enzyme electrode.

According to this method, however, when glucose concentration of the sample is comparatively high, because of converting sucrose to glucose on the second enzyme electrode, a great amount of the electrode active material is formed. Therefore, the amount exceeds the range, in which the amount of the electrode active material is proportional to the output current. Thus, an accurate value of sucrose concentration can not be obtained.

In this case, by using the second enzyme electrode having reduced amount of immobilized enzymes and lower sensitivity, the sample of high substance concentration is able to be analyzed. On the other hand, in this method, one must prepare the electrodes of different sensitivity corresponding to concentration of substances in the sample solution. So the apparatus employing this method is not practical at all.

SUMMARY OF THE INVENTION

It is an object of the invention to provide a measuring apparatus which gives accurate value of concentrations of a plural kinds of substances in a sample, in a short time.

The above and other characteristics and advantages of the invention will be better understood through the following illustrative and non-limitative description.

In order to accomplish the foregoing objects, the invention provides a measuring apparatus having enzyme electrodes comprising;

means for supplying a buffer solution continuously at a predetermined flow rate, means for injecting intermittently a sample containing at least one of a first substance to be measured and a second substance to be measured into the flow of the buffer solution, a first enzyme electrode situated downstream with respect to the injecting means and for detecting the first substance, a dilution pipeline situated at the downstream of the first enzyme electrode and for diluting the sample along to the direction of the flow, and a second enzyme electrode, situated downstream with respect to the dilution pipeline, having an immobilized enzyme for catalyzing to convert the second substance into the first substance, and for detecting (a) the first substance originally contained in the sample and (b) the first substance converted from the second substance.

In a preferred embodiment of the invention, the dilution pipeline has a flow path of an inner diameter of 0.1–2.0 mm and an axial length of 20–1000 cm.

Preferably, the dilution pipeline is made of synthetic resin or stainless steel.

More preferably, the dilution pipeline is coiled.

In another preferred embodiment of the invention, there is provided a plurality of dilution pipelines, each of which has a different inner diameter and/or a different axial length respectively, and a valve situated to connect selectively one of the dilution pipelines between the first enzyme electrode and the second enzyme electrode.

In one embodiment of the invention, the first enzyme electrode having an immobilized enzyme of glucose oxidase, and the second enzyme electrode having immobilized enzymes of glucose oxidase, mutarotase and invertase.

In another embodiment of the invention, the first enzyme electrode having an immobilized enzyme of glucose oxidase, and the second enzyme electrode having immobilized enzymes of glucose oxidase, mutarotase and α-glucosidase.

In another embodiment of the invention, the first enzyme electrode having an immobilized enzyme of glucose oxidase, and the second enzyme electrode having immobilized enzymes of glucose oxidase and β-glucosidase.

In another embodiment of the invention, the first enzyme electrode having an immobilized enzyme of glucose oxidase and the second enzyme electrode having immobilized enzymes of glucose oxidase and glucoamylase.

In another embodiment of the invention, the first enzyme electrode having an immobilized enzyme of glucose oxidase, and the second enzyme electrode having immobilized enzyme of glucose oxidase and lactase.

In another embodiment of the invention, the first enzyme electrode having an immobilized enzyme of cholesterol oxidase and, the second enzyme electrode having immobilized enzymes of cholesterol oxidase and cholesterol esterase.

The invention provides a measuring method using enzyme electrodes comprising steps of;

supplying a constant flow of a buffer solution, preparing (a) a first enzyme electrode for detecting a first substance to be measured, (b) a dilution pipeline situated downstream with respect to the first enzyme electrode, and (c) the second enzyme electrode situated downstream with respect to the dilution pipeline, for converting a second substance to be measured into the first substance, and for detecting the first substance, injecting the first substance into the flow of the buffer solution upstream with respect to the first enzyme electrode intermittently, calculating a response ratio k1, which is represented by the following equation (1), $$k1 = ib / ia \qquad (1)$$

wherein output current value of the first enzyme electrode is represented by ia and output current value of the second enzyme electrode is represented by ib, injecting a sample to be analyzed containing at least one of the first substance and the second substance into the flow of the buffer solution upstream with respect to the first enzyme electrode intermittently, and calculating a measured value i3 of the second substance, which is represented by following equation (2), $$i3 = i2 - k1 \cdot i1 \qquad (2)$$

wherein output current value of the first enzyme electrode is represented by i1, and output current value of the second enzyme electrode is represented by i2.

According to the invention, in a flow-type measuring apparatus, a sample is injected into a constant flow of buffer solution, and the apparatus is provided with (a) a first enzyme electrode to face the constant flow to measure a first substance, for example glucose (b) a dilution pipeline situated downstream of the first enzyme electrode, and (c) a second enzyme electrode situated downstream and for detecting for example sucrose, as a second substance and glucose. Therefore, as the substances in the sample is automatically diluted through the dilution pipeline, the second enzyme electrode is able to be responsive to higher concentration of the substances proportionally. So the concentrations of the plural kinds of substances can be measured accurately.

As described above, the invention is an excellent measuring apparatus that is able to accomplish accurate measurement of plural kinds of substances easily and immediately.

BRIEF DESCRIPTION OF THE DRAWINGS

Detailed description of the invention will be made with reference to the accompanying drawings, in which.

DETAILED DESCRIPTION OF THE PREFERRED EMBODIMENTS

The detailed description that will follow represents the best considered modes for carrying out the invention. It is understood that the following description should not be interpreted in any restrictive sense, since it is intended to illustrate general concept of the invention, and the scope of the invention should be defined by the appended claims.

Figure 1:
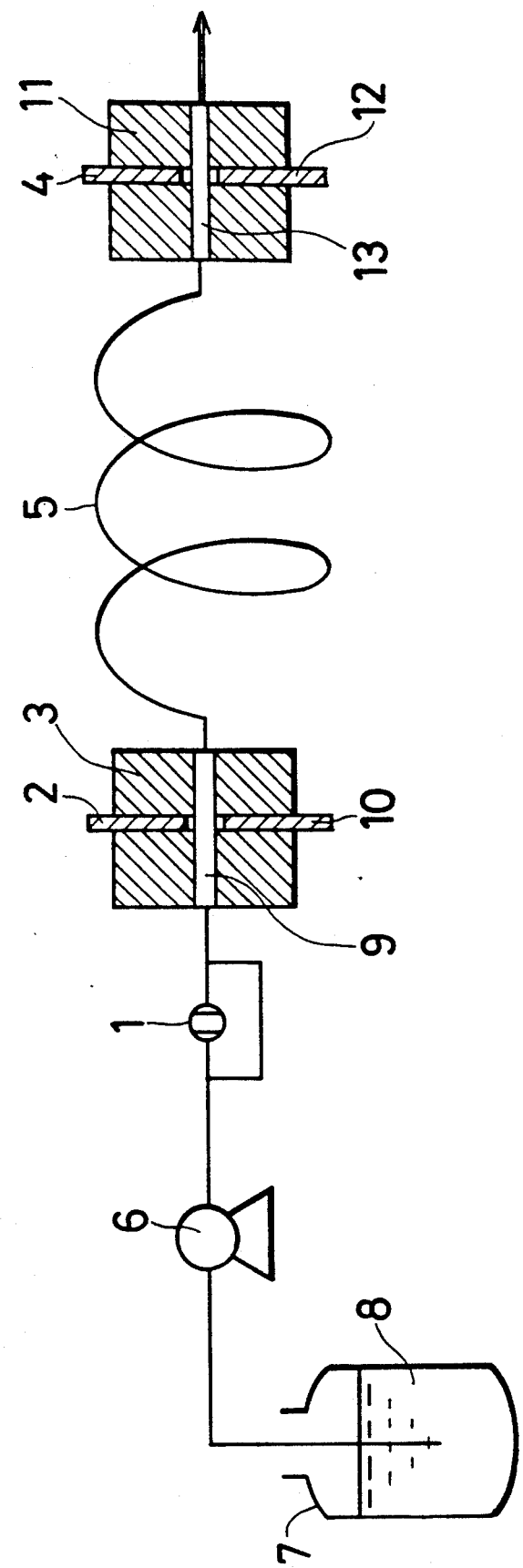
FIG. 1 is a system diagram showing a measuring apparatus having enzyme electrodes 2, 4 which represents one embodiment of the invention.

Referring to FIG. 1 showing the measuring apparatus of the invention, buffer solution 8 stored in a vessel 7 is supplied through a pump 6 at a predetermined rate of flow. The buffer solution from the pump 6 is caused to flow into measuring cell 3 through an injector 1. For example, an injector, which is generally used of high performance liquid chromatography, is preferably used as the injector 1. Samples to be introduced through the injector 1 contain two substances, i.e., a first substance to be measured (for example, glucose) and a second substance to be measured (for example, sucrose). A first enzyme electrode 2 and a reference electrode 10 are disposed in opposed relation facing a flow path 9 formed in the measuring cell 3. A dilution pipeline 5 is connected to the downstream side of the measuring cell 3. The measuring cell 3 is sometimes referred to as "first measuring cell" hereinafter. This pipeline 5 preferably has a flow path of an inner diameter of the order of 0.1-2.0 mm and an axial length of the order of 20-1000 cm, so that the first and second substances to be measured are prevented from being diffused and diluted in the buffer solution over an excessively wide range in the axial direction of the pipeline 5, it being thus possible to allow effective dilution to be performed at high speed. The axial length of the pipeline 5 is suitably adjusted according to the concentration ratio of the first substance with the second substance to be measured. If the length is too short, no sufficient effect of dilution can be taken, and if it is too long, considerable time is required for measurement. Therefore, the axial length of the pipeline 5 should, as above indicated, be preferably of the order of 20-1000 cm, more preferably 50-300 cm. The pipeline 5 may be made of fluoric resin, such as Teflon, or such other synthetic resin as polyvinyl chloride, or may be made of a metallic material, such as stainless steel. In order to allow efficient mixing the first and second substances with the buffer solution, the pipeline 5 is configured to be of a coil shape.

A second measuring cell 11 is connected to the downstream end of the dilution pipeline 5. In the second measuring cell 11., a second enzyme electrode 4 and a reference electrode 12 are disposed in face-to-face relation each other across a flow path 13. In order to prevent wide variation of measured peak values at the enzyme electrodes 2, 4, the capacity of each of the flow paths 9, 13 of the measuring cells 3, 11 is preferably of the order of 5-100 $\mu$l.

The first enzyme electrode 2 detects said first substance.

The second enzyme electrode 4 exhibits enzyme reactions to produce said first substance from said second substance and also detects said first substance.

Where said first substance is glucose and said second substance is sucrose, the first enzyme electrode 2 is an electrode having glucose oxidase immobilized thereon, and the second enzyme electrode 4 is an electrode having glucose oxidase, mutarotase, and invertase immobilized thereon.

Where said first substance is glucose and said second substance is maltose, the first enzyme electrode 2 is an electrode having glucose oxidase immobilized thereon and the second enzyme electrode 4 is an electrode having glucose oxidase, mutarotase, and $\alpha$-glucosidase immobilized thereon.

Where said first substance is glucose and said second substance is $\beta$-glucoside, the first enzyme electrode 2 is an electrode having glucose oxidase immobilized thereon and the second enzyme electrode 4 is an electrode having glucose oxidase and $\beta$-glucosidase immobilized thereon.

Where said first substance is glucose and said second substance is maltooligosugars, the first enzyme electrode 2 is an electrode having glucose oxidase immobilized thereon and the second enzyme electrode 4 is an electrode having glucose oxidase and glucoamylase immobilized thereon.

Where said first substance is glucose and said second substance is lactose, the first enzyme electrode 2 is an electrode having glucose oxidase immobilized thereon and the second enzyme electrode 4 is an electrode having glucose oxidase and lactase immobilized thereon.

For purposes of detecting free cholesterol and ester-type cholesterol, the first enzyme electrode 2 is an electrode having cholesterol oxidase immobilized thereon and the second enzyme electrode 4 is an electrode having cholesterol oxidase and cholesterol esterase immobilized thereon.

Figure 2:
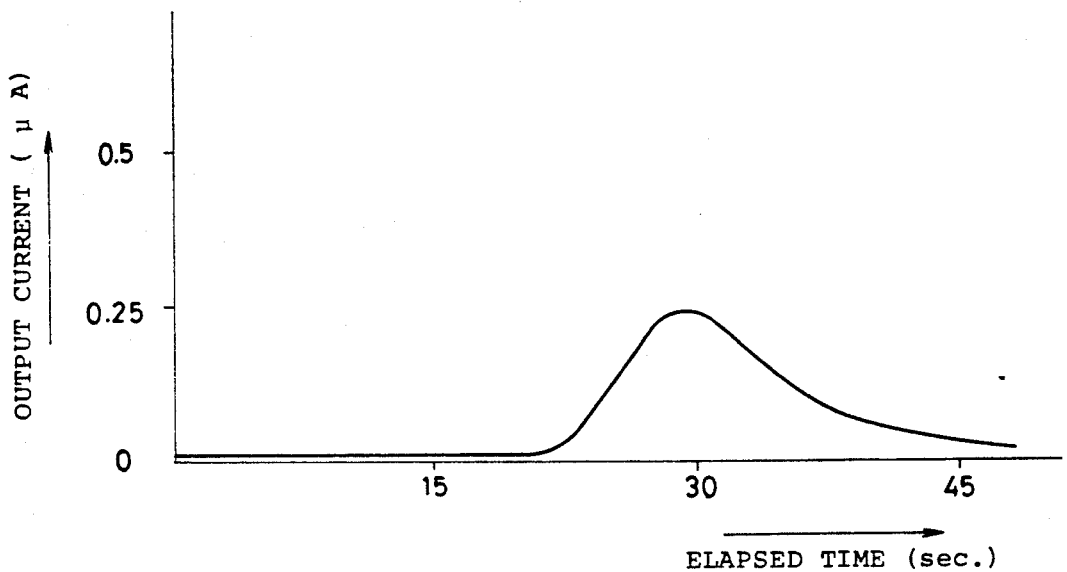
FIG. 2 is a graph showing the response curve of the second enzyme electrode 4 in response to glucose in the embodiment.
Figure 3:
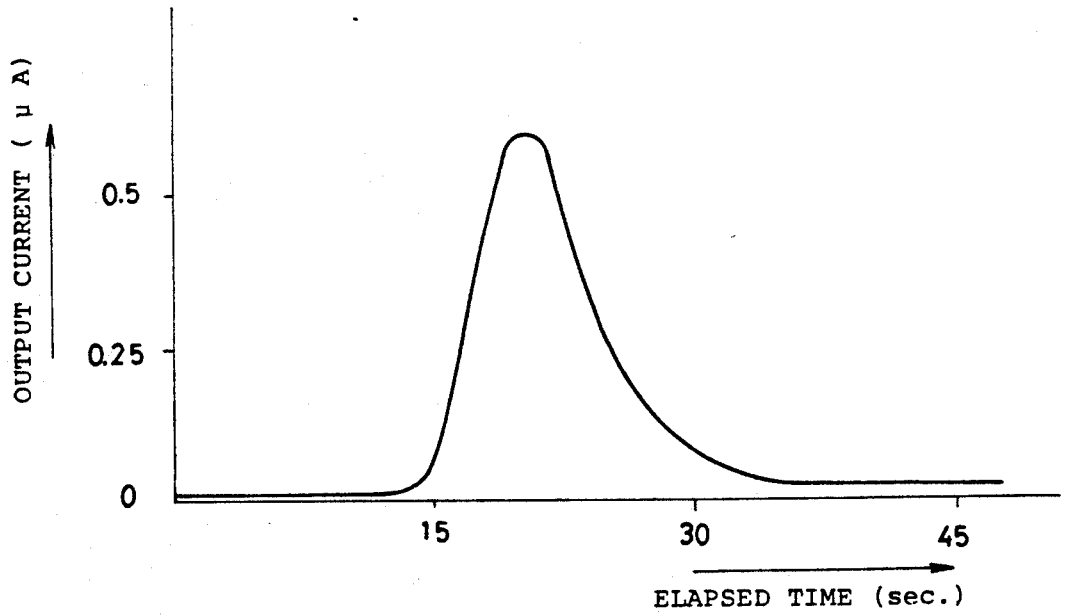
FIG. 3 is a graph showing the response curve of the second enzyme electrode 4 in response to glucose without using the dilution pipeline 5.

A characteristic feature of the present invention is that, after measurement of said first substance by the first enzyme electrode 2, a sample leaving the first measuring cell 3, that is a mixture solution of said first and/or second substance and the buffer solution, is guided into the dilution pipeline 5 so that said first and second substances are diffused and diluted in the buffer solution within the dilution pipeline 5. For example, when glucose as said first substance to be measured is injected through the injector 1 and the same is detected by the second enzyme electrode 4, a response curve as shown in FIG. 2 can be obtained, in which a maximal output current value from the second enzyme electrode 4 is comparatively small, so that said first and second substances of high concentration can be effectively measured. In contrast, if a buffer solution containing said first and/or second substance to be measured is guided directly into the second measuring cell 11 without using the dilution pipeline 5, a maximal output current value from the second enzyme electrode 4 is considerably high as shown in FIG. 3. As a consequence, the concentration of said first substance detected by the second enzyme electrode 4 deviates from upper limit of its proportional range, and thus it is unlikely to perform accurate measurement of said second substance. The dilution pipeline 5 eliminates this problem.

Generally, a proportional range of the concentration of a substance to be measured in relation to the value of output current from an enzyme electrode is determined by kinetic constants, diffusion constant of the to-be-measured substance in an immobilized enzyme layer and, where oxygen is required as is the case with the immobilized enzyme being oxidase, the amount of dissolved oxygen. Therefore, if the concentration of said first substance as measured by the second enzyme electrode 4 is excessively high, it is likely to deviate from aforesaid proportional range, it being thus impracticable to perform accurate measurement of the concentration of said first substance.

Figure 4:
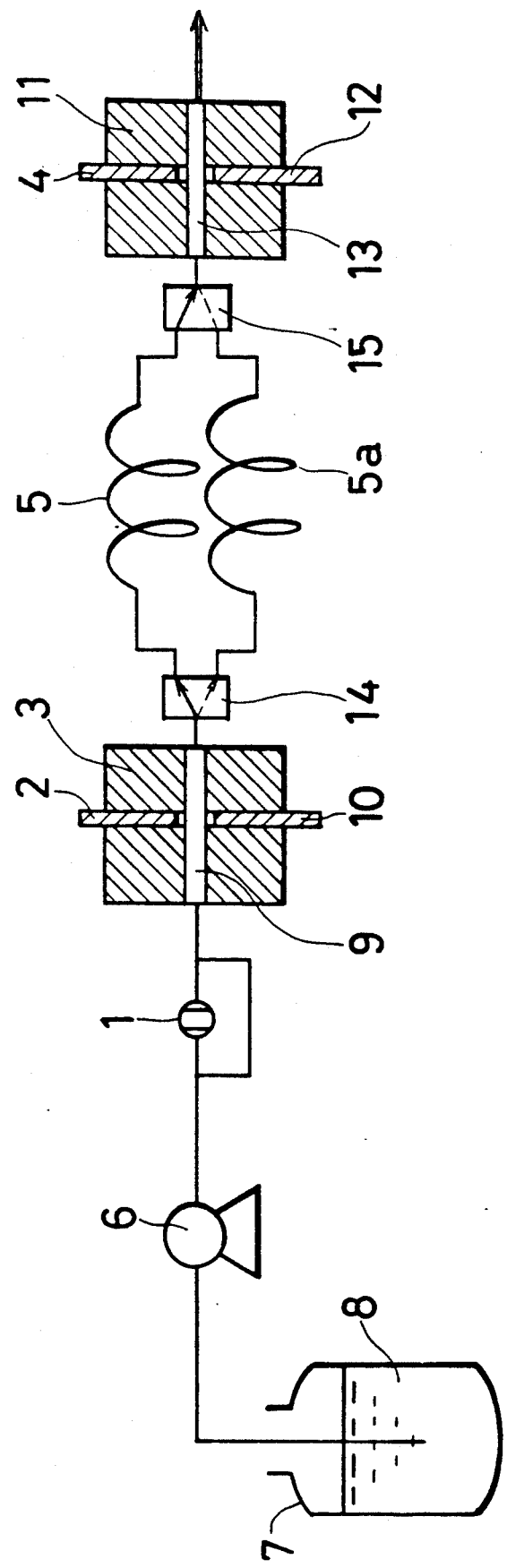
FIG. 4 is a system diagram showing another embodiment of the invention.

Referring to FIG. 4, there is shown another embodiment of the invention, which is applicable in the case where said first and second substances to be measured are considerably different in concentration, wherein a plurality of dillution pipelines 5, 5a (two in number in FIG. 4) are provided so that they may be changed over from one to the other by means of valves 14, 15. The dilution pipelines 5, 5a are different in dimensional configuration, such as flow path inner diameter and axial length. The dilution pipelines 5, 5a may be adapted to be interchangeably connected to the measuring cells 3, 11 by means of pipe joints, instead of being provided with valves 14, 15.

In the FIG. 1, the measuring apparatus in accordance with the invention, while the buffer solution is supplied by the pump 6 at constant flow rate, said first substance to be measured is intermittently injected by means of the injector 1 for mixture with the buffer solution. In this case, the first enzyme electrode 2 gives such characteristic relation as indicated by line 11 in FIG. 5 and the second enzyme electrode 4 gives such characteristic relation as indicated by line 12 in FIG. 5. Where, within the proportional range of the concentration of said first substance at the first and second enzyme electrodes 2, 4 in relation to output current values from the electrodes, when molarity of the first substance is represented by Ma, output current value of the first enzyme electrode 2 is represented by ia and output current value of the second enzyme electrode 4 is represented by ib, a response ratio k1 is calculated according to the following relation:

$$K1 = ib/ia \qquad (1)$$

Next, samples of said first substance of a predetermined concentration mixed with said second substance of varied concentrations are intermittently introduced from the injector 1. As a consequence, the first enzyme electrode 2 exhibits such characteristic relation as indicated by line 14 in FIG. 6 and the second enzyme electrode 4 exhibits such characteristic relationship as indicated by line 15 in FIG. 6. Where, in FIG. 6, the output of the first enzyme electrode 4 is represented by i1 and the output of the second enzyme electrode 4 is represented by i2, output current i3 of the second enzyme electrode 4 due to said second substance only is as shown by line 16 in FIG. 7, which is expressed by the following formula. Output current i3 is proportional to the concentration of said second substance.

$$i3 = i2 - k1 \cdot i1 \qquad (2)$$

According to the invention, as above described, automatic dilution of samples take place in the dilution pipeline 5 between two enzyme electrodes 2 and 4, so that the proportional range at the second enzyme electrode can be extended, it being thus possible to measure samples of varied concentrations with good accuracy and in short time. Unlike any apparatus based on the flow injection technique using columns, the measuring apparatus of the invention does not require any change of flow path, and therefore it has an advantage that changes in divisional flow ratio due to variations in back pressure or joint portion dead capacity need not be considered.

EXAMPLE 1

For the first enzyme electrode 2 in FIG. 1, glucose detecting electrode having glucose oxidase immobilized thereon is employed, and for the second enzyme electrode 4, a glucose and sucrose detecting electrode having glucose oxidase, invertase, and mutarotase immobilized thereon is employed.

Preparation of Enzyme Electrodes 2, 4

On the surface of a thoroughly cleaned platinum electrode having a diameter of 2 mm was put dropwise 5 μl of an aqueous solution containing 3 mg/ml of glucose oxidase (Type II, produced by Sigma), 7 mg/ml of bovine serum albumin ("Fraction V", produced by Sigma), and 0.5 wt % of glutaraldehyde, and was treated at 40° C. for 30 minutes, thereby glucose oxidase was immobilized on the surface. This electrode was employed as a first enzyme electrode 2.

On the surface of a platinum electrode was put dropwise 5 μl of an aqueous solution containing 3 mg/ml of glucose oxidase, 1.5 mg/ml of invertase (grade X, Candida utilis, made by Sigma), 0.1 mg/ml of mutarotase (produced by Sigma), 5.4 mg/ml of bovine serum albumin, and 0.5 wt % of glutaraldehyde, and was treated at 40° C. for 30 minutes, the enzymes were thereby immobilized to the surface. This electrode was employed as a second enzyme electrode 4.

The measuring apparatus employed (FIG. 1) was of such arrangement that an injector 1, which is generally used for high performance liquid chromatograph and is capable of injecting samples on the order of microliters (μl), and a measuring cell 3 having the first enzyme electrode 2 mounted therein were interconnected by a Teflon tube having an inner diameter of 0.5 mm and a length of 1.5 m. The measuring cell 3 was connected to a measuring cell 11 for the second enzyme electrode 4 by a Teflon-made dilution pipeline 5 (of spiral form, with an outer diameter of 2.8 cm) having an extended length of 2.0 m and an inner diameter of 0.5 mm. The measuring cells 3, 11 each had an internal volume of 40 μl, and in their interior there were disposed Ag/AgCl reference electrodes 10, 12 respectively in opposed relation to the enzyme electrodes 2, 4. To each of the enzyme electrodes 2,4 was applied a voltage of +0.45V for the corresponding Ag/AgCl reference electrode. For supplying a buffer solution, a high performance liquid chromatograph pump was used as a pump 6, and a buffer solution of 0.1M sodium phosphate at pH 7.0 was supplied at a flow rate of 1.0 ml/min.

Figure 5:
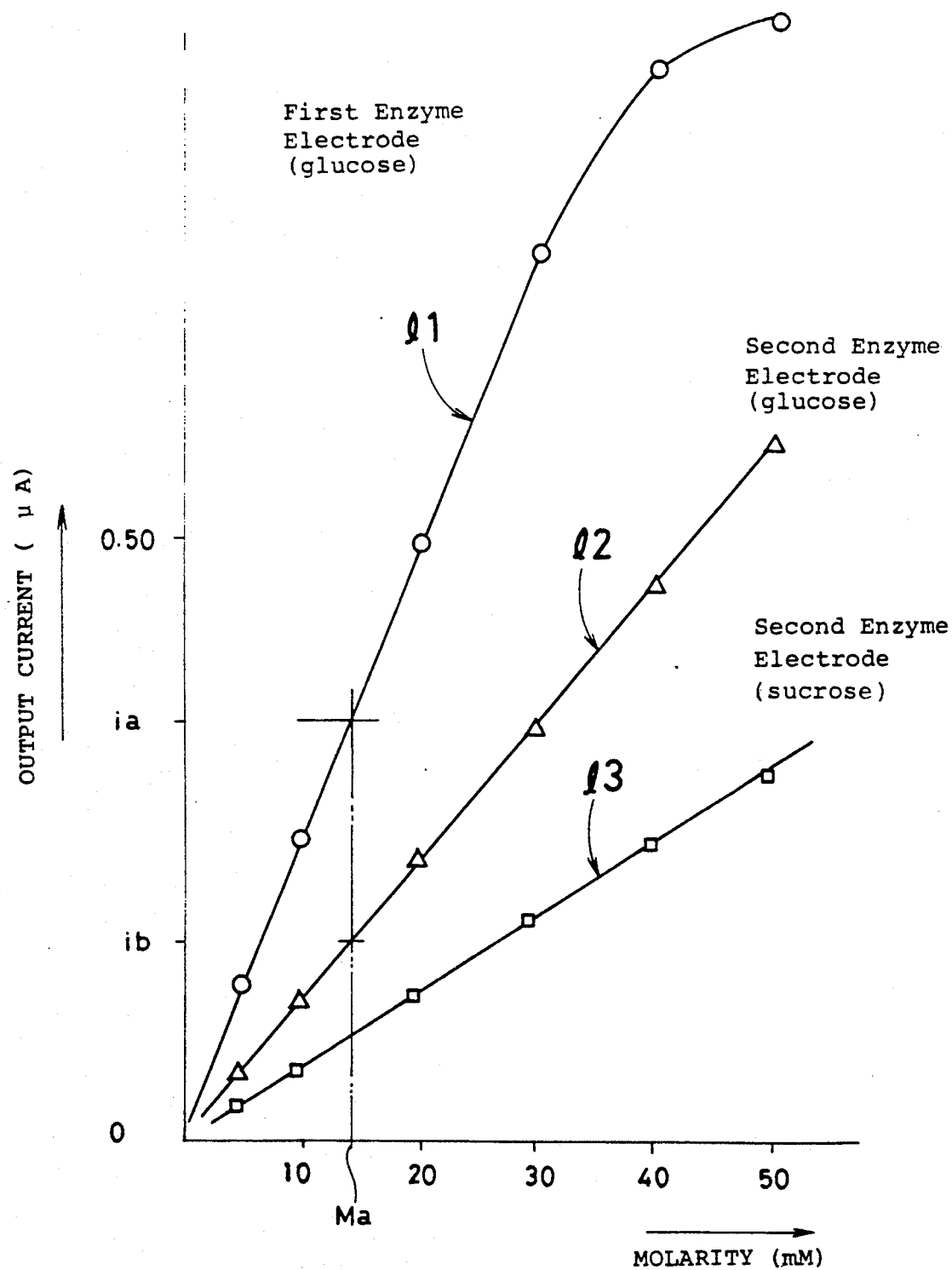
FIG. 5 is a graph showing the output current values of the first and second enzyme electrodes 2, 4 in response to glucose and sucrose in Example 1.
Figure 6:
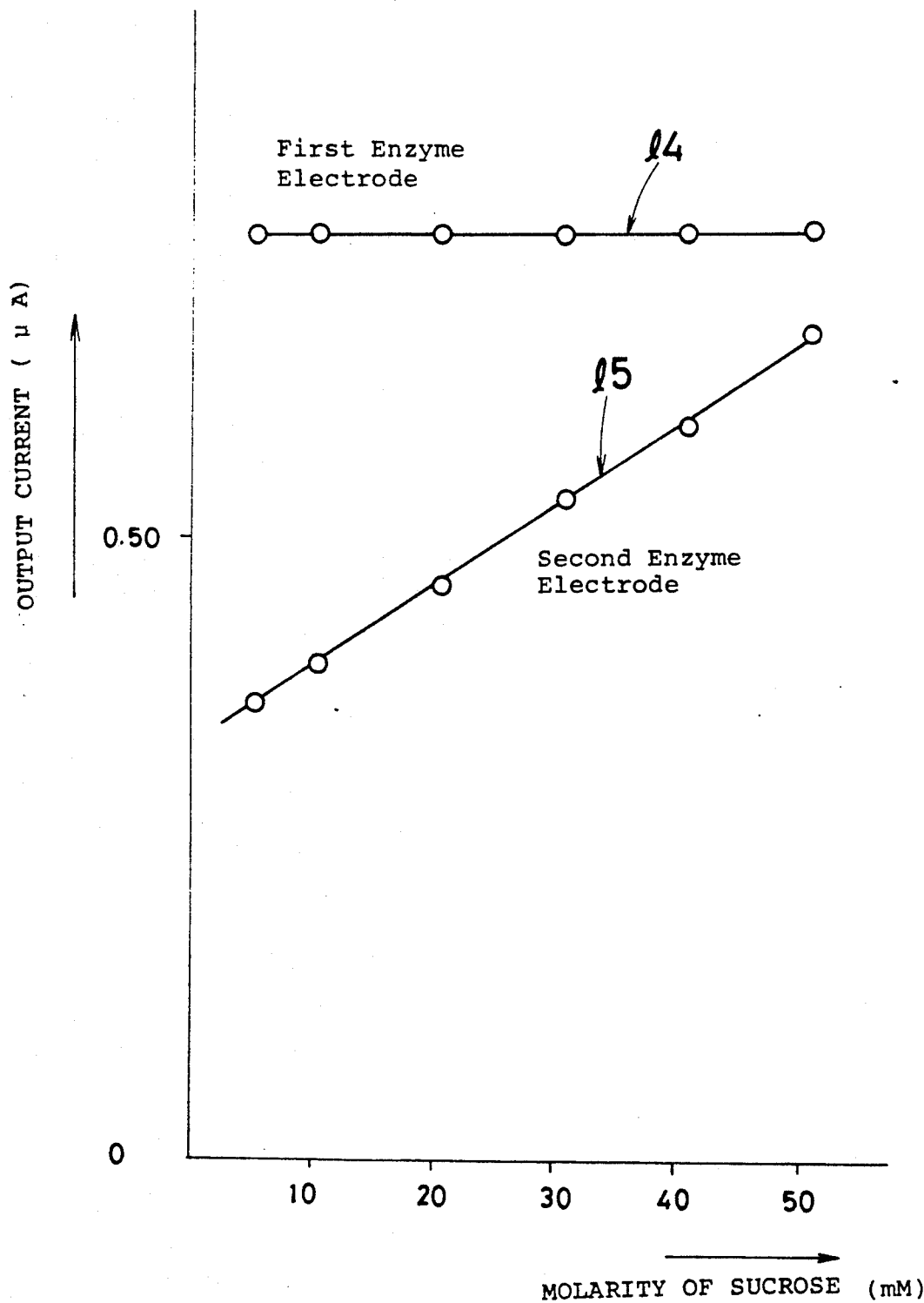
FIG. 6 is a graph showing the output current values of the first and second enzyme electrodes 2, 4 in response to the sample of 30 mM glucose and varied concentration of sucrose.
Figure 7:
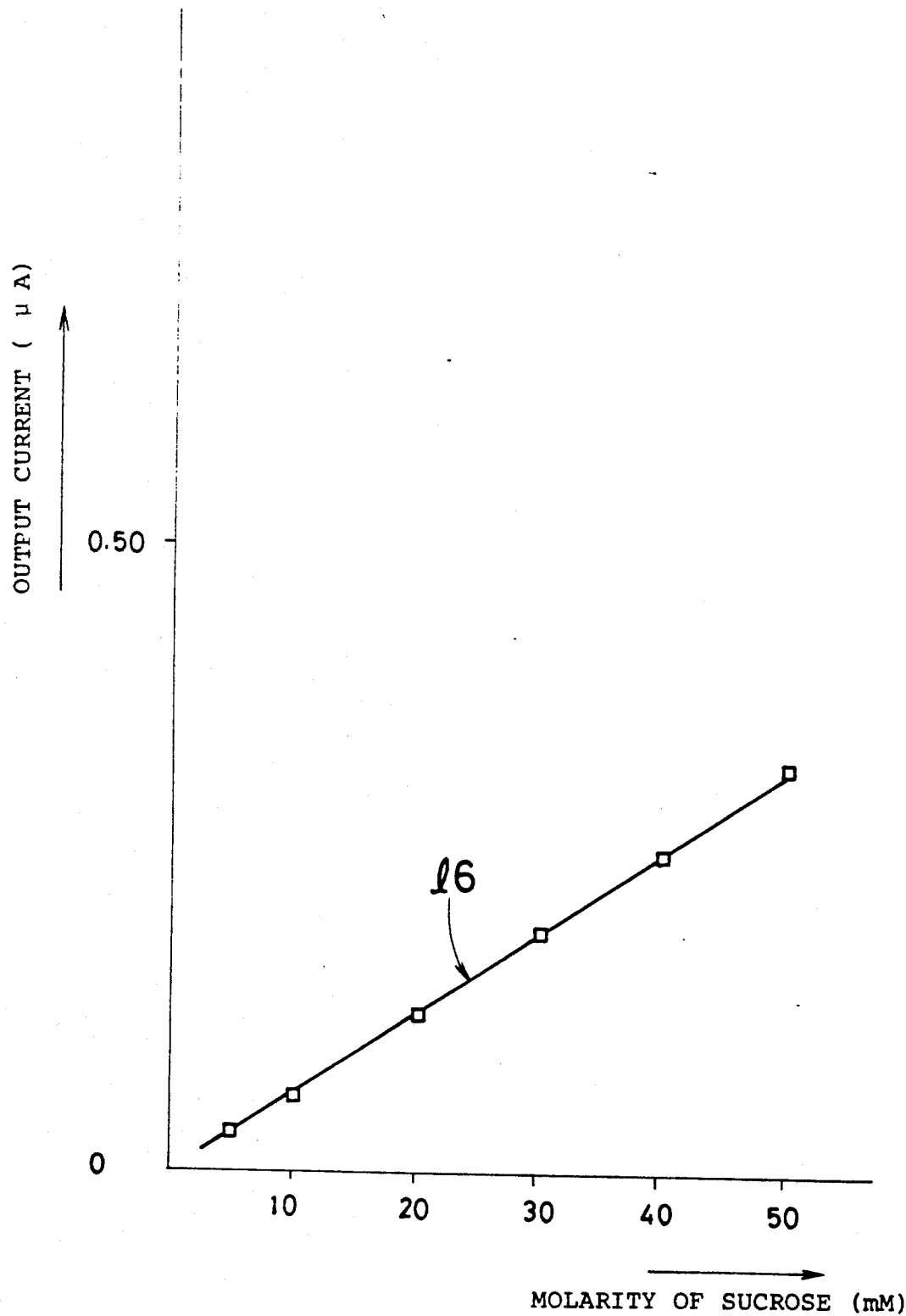
FIG. 7 is a graph showing a calibration curve of sucrose in Example 1.

In this system, an aqueous solution of glucose only (with a concentration range of 5-50 mM) and an aqueous solution of sucrose only (with a concentration range of 5-50 mM) were first injected in the amount of 5 μl each, and thus individual calibration curves 11-13 were obtained (as earlier described with references to FIG. 5). With the first enzyme electrode 2, the linear range of glucose was up to 30 mM. Nextly, sucrose concentration varied samples, each of which contains 30 mM of glucose (with sucrose concentration 5-50 mM) were prepared, and calibration curves 14, 15 were obtained as shown in FIG. 6. The response ratio k1 of the first enzyme electrode 2 and the second enzyme electrode 4 in relation to glucose was determined from the calibration curves 11, 12 (in FIG. 5, the ratio between output of the first enzyme electrode 2 and output of the second enzyme electrode 4 in relation with glucose is 0.46), by which the calibration curve 15 in FIG. 6 for glucose-added sucrose was amended as shown in FIG. 7. Thus, a calibration curve 16 in FIG. 7 for sucrose which is free from the influence of glucose was obtained from the outputs of the first and second enzyme electrodes 2, 4. The calibration curve 16 agreed with the calibration curve 13 in FIG. 5.

Where, in FIG. 6, the output of the second enzyme electrode 4 with respect to glucose and sucrose is represented by i2 and the output of the first enzyme electrode 2 with respect to glucose is represented by i1, FIG. 7 shows a calibration curve for output i3 relative to sucrose concentration, that is, values for (i2−0.46·i1), by which curve a value for sucrose concentration can be determined. Even where the second enzyme electrode contains glucose of 30 mM, its linear detectable range for sucrose is up to 50 mM, from which fact it can be seen that even samples of high concentration are well detectable.

COMPARATIVE EXAMPLE 1

Figure 8:
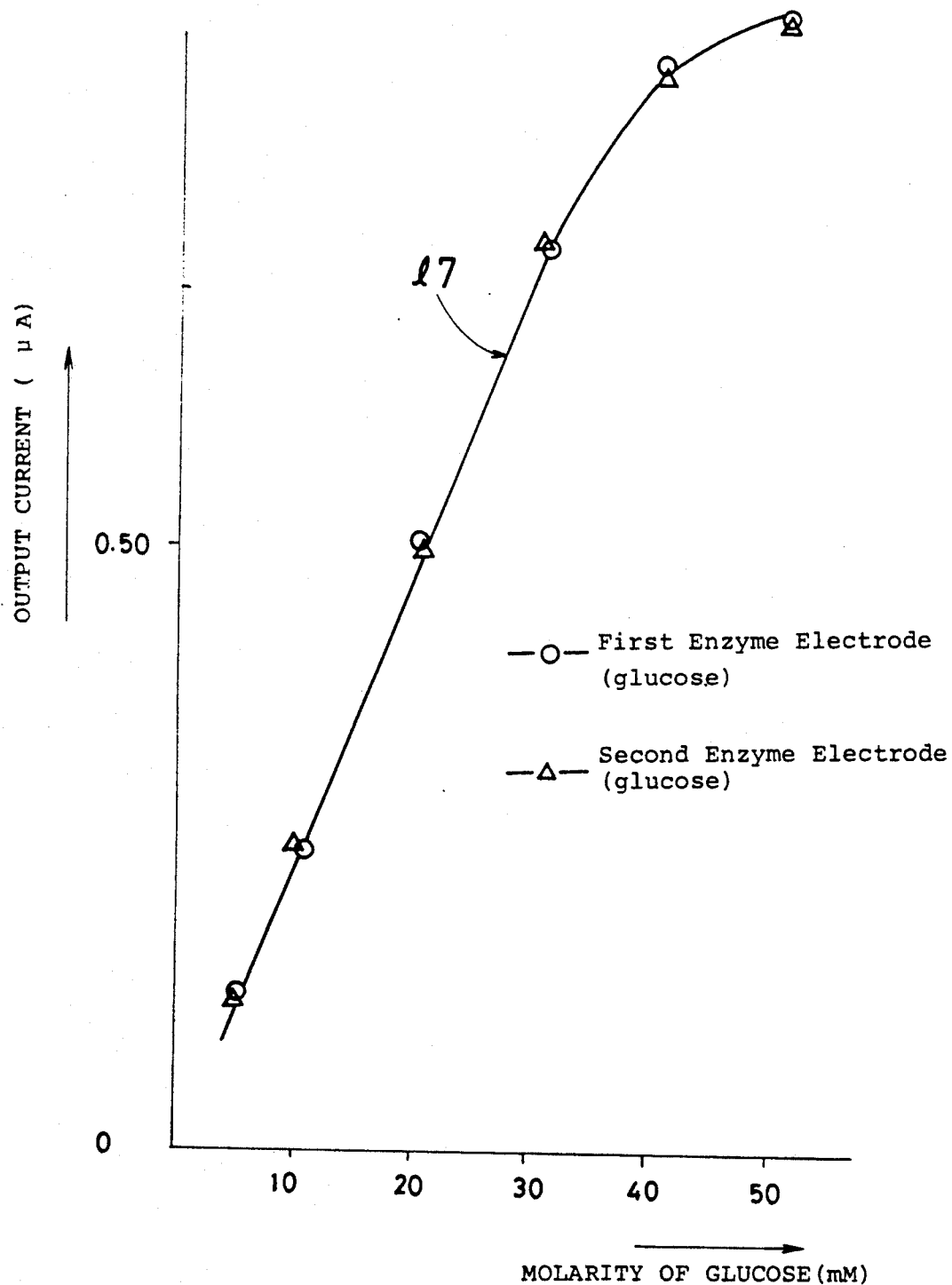
FIG. 8 is a graph showing the output current values of the first and the second enzyme electrodes 2, 4 in response to glucose without using the dilution pipeline 5 in Comparative Example 1.

Without using the dilution pipeline 5 in FIG. 1, the first and second enzyme electrodes 2, 4 were respectively mounted in the measuring cells 3, 11, and measurement was carried out in the same manner as in Example 1. The calibration curve 17 of the electrodes 2, 4 relative to glucose were both saturated at 30 mM, as shown in FIG. 8. That is, with samples containing glucose of 30 mM and sucrose, outputs of the second enzyme electrode were outside a linear range and, therefore, no accurate measurement was possible.

EXAMPLE 2

For the enzyme electrode 2 in FIG. 1, a glucose detecting electrode having glucose oxidase immobilized thereon was employed, and for the second enzyme electrode 4, a glucose and maltooligosugars detecting electrode having glucose oxidase and glucoamylase (Rhizopus, made by Sigma) immobilized thereon was employed. The first enzyme electrode was of the same construction as the one used in Example 1. The second enzyme electrode 4 was prepared in the same manner as in Example 1 except using different kind of enzyme. Other aspects of arrangement were the same as those in Example 1.

Figure 9:
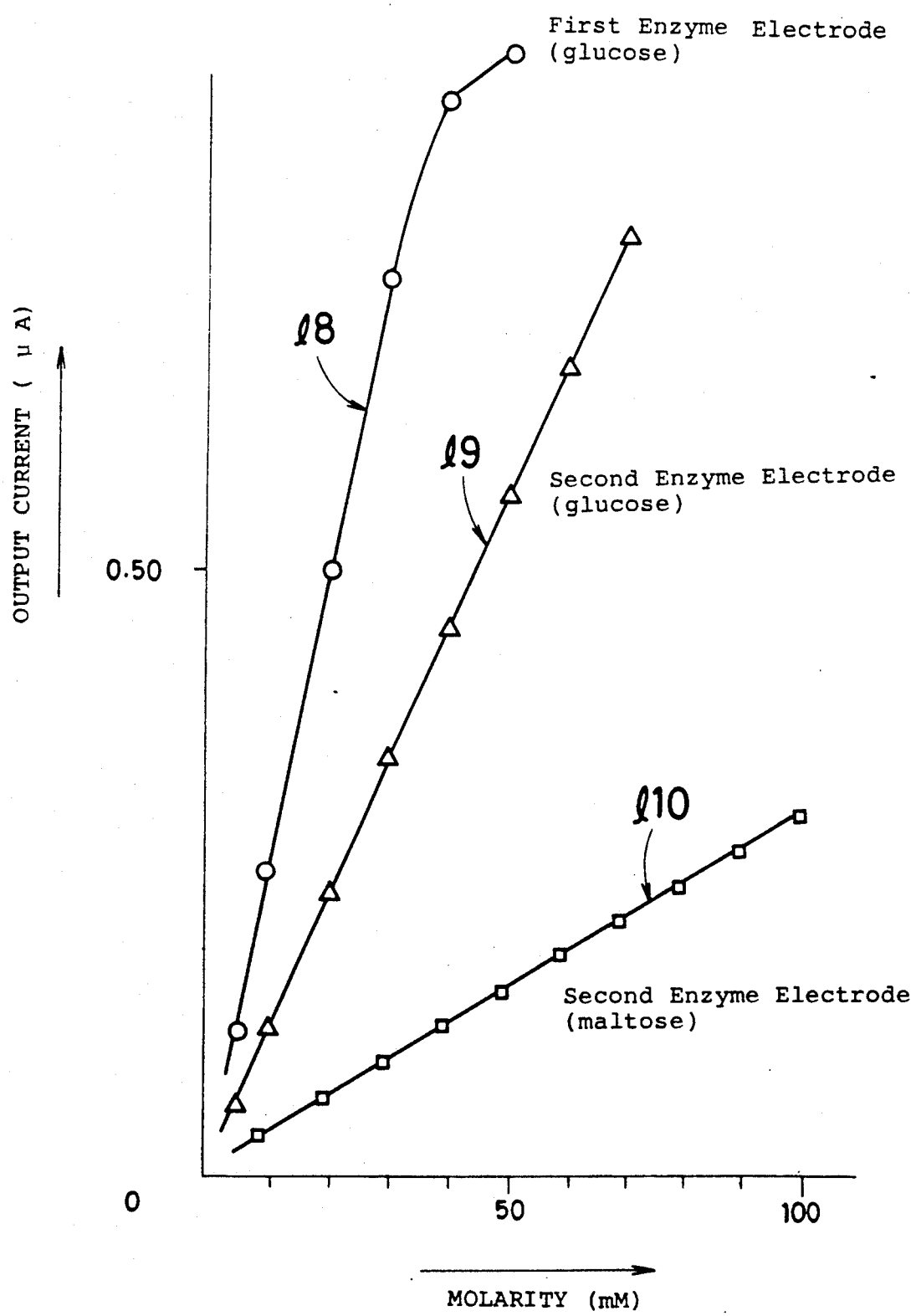
FIG. 9 is a graph showing the output current values of the first and second enzyme electrodes 2, 4 in response to glucose and maltose in Example 2.

According to the same procedure as used in Example 1 as aqueous solution of glucose only was first introduced through the injector 1 and a carbration curve as shown by line 18 in FIG. 9 was obtained. A calibration curve as shown by line 19 was obtained from the second enzyme electrode 4. Then, maltose only was introduced through the injector 1 and a calibration curve shown by 110 was obtained.

Figure 10:
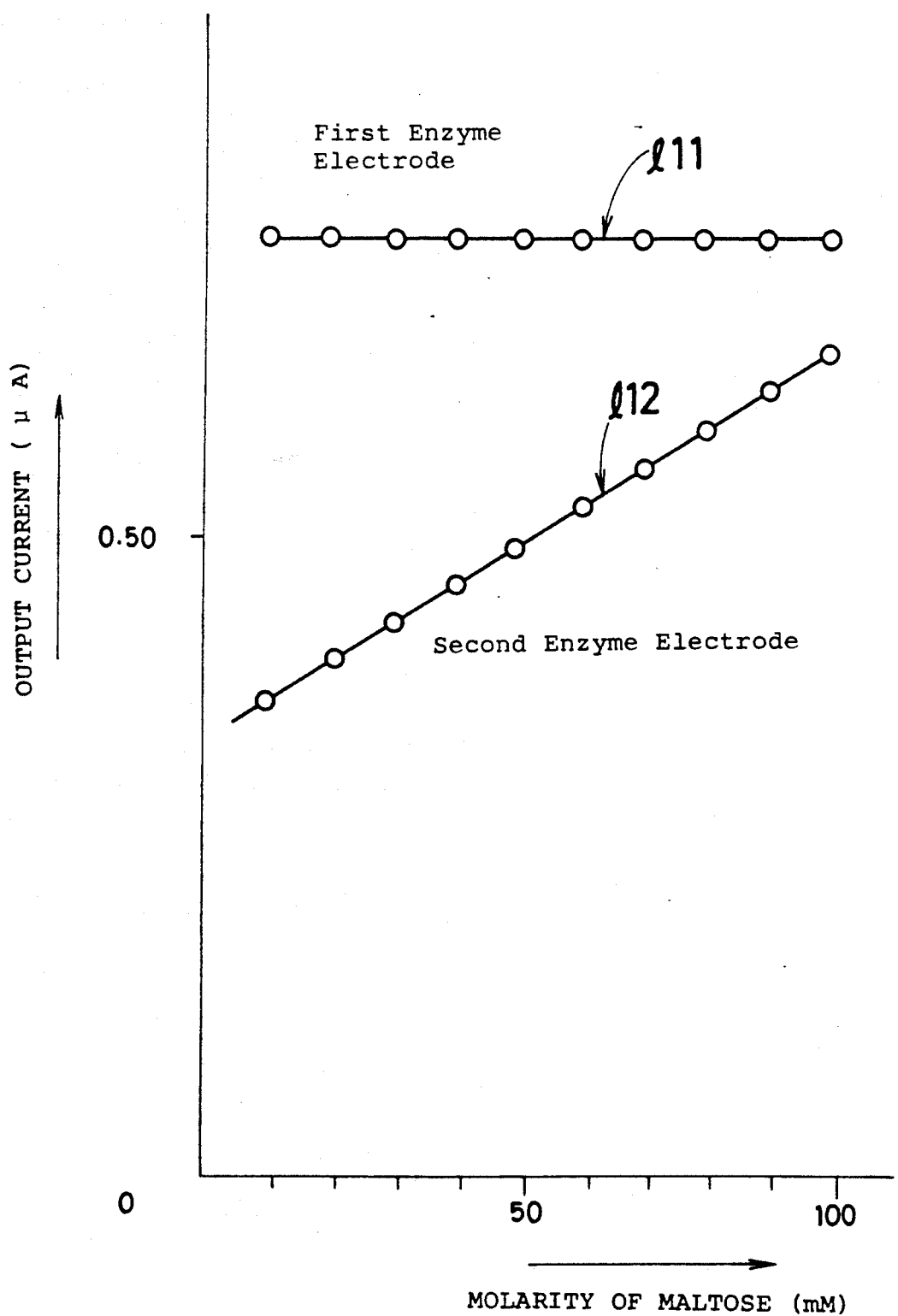
FIG. 10 is a graph showing the output current values of the first and second enzyme electrodes 2, 4 in response to the sample of 30 mM glucose and varied concentration of maltose in Example 2.
Figure 11:
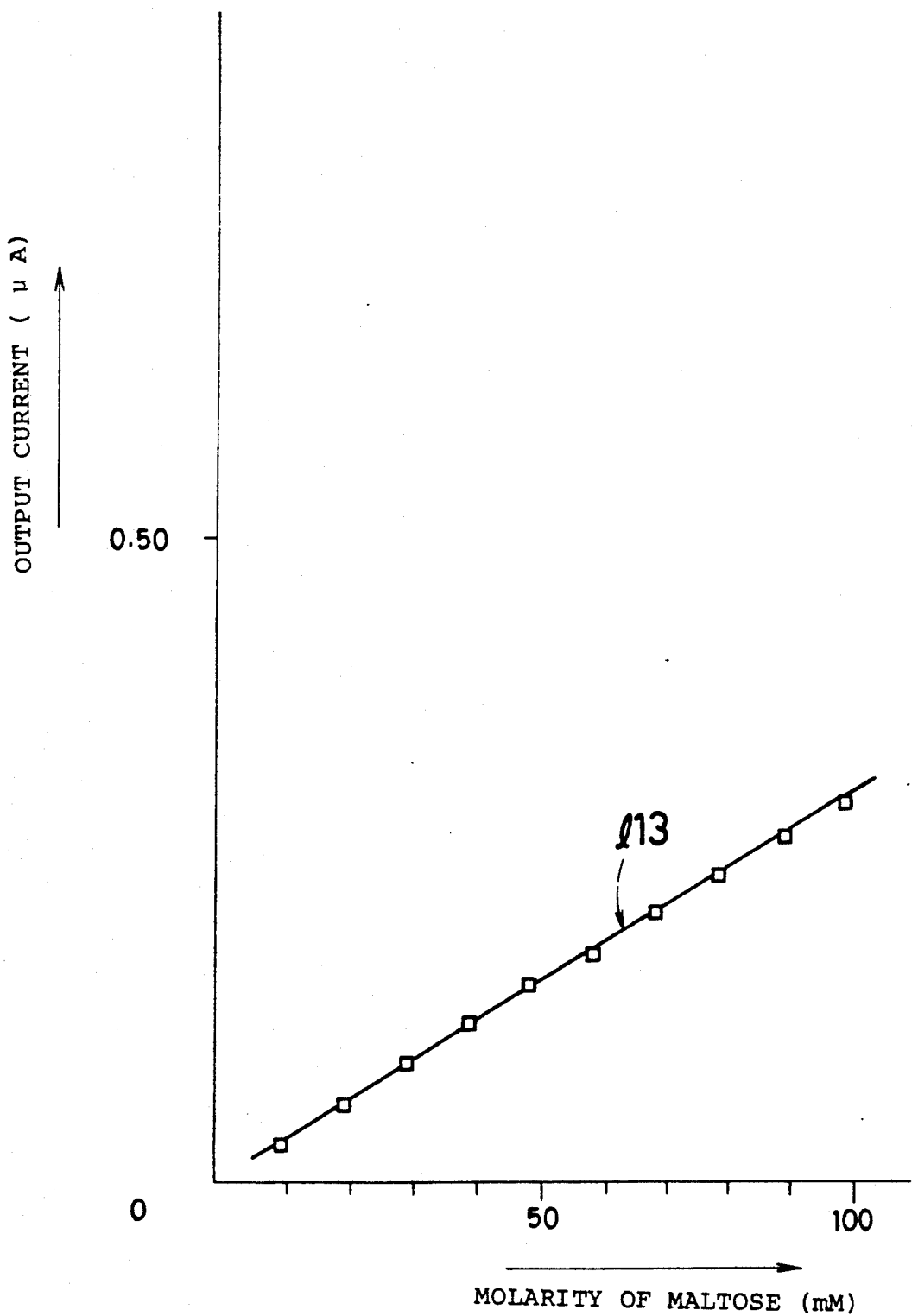
FIG. 11 is a graph showing a calibration curve of maltose in Example 2.

Maltose solutions (with a maltose concentration range of 5-100 mM) containing 30 mM of glucose were prepared, and such characteristic representation as shown by line 111 in FIG. 10 was obtained with the first enzyme electrode 2 and such characteristic representation as shown by line 112 with the second enzyme electrode 4. From these characteristic lines and according to the foregoing equations (1) and (2) it is possible to obtain a calibration curve 113 indicating the relationship between the concentration of maltose and output current value of the second enzyme electrode 4 due to maltose only can be obtained as shown in FIG. 11.

COMPARATIVE EXAMPLE 2

Figure 12:
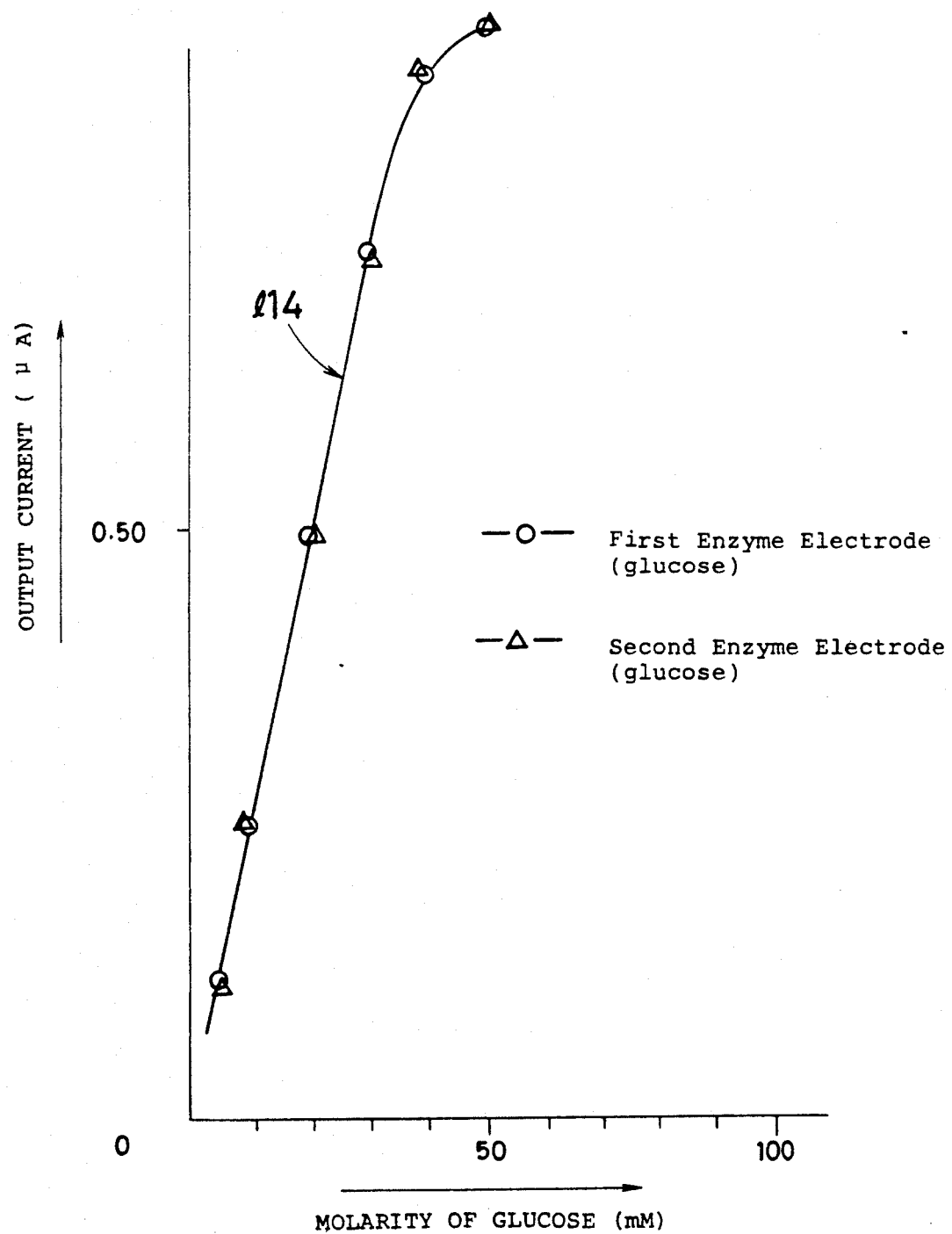
FIG. 12 is a graph showing the output current values of the first and second enzyme electrodes 2, 4 in response to glucose without using the dilution pipeline 5 in Comparative Example 2.

Without using the dilution pipeline 5 in Example 2, the first and second enzyme electrodes 2, 4 were respectively mounted in the measuring cells 3, 11, and measurement was carried out in the same manner as in Example 2. A calibration curve as shown by line 1 14 in FIG. 12 was obtained. The output currents of the first and second enzyme electrodes 1 and 2 came to saturation at a glucose concentration of 30 mM. Therefore, with samples containing glucose of 30 mM and maltose, the output of the second enzyme electrode deviated from its measurable proportional range, and it was unable to perform accurate measurement of maltose concentration.

Thus, Example 1, Comparative Example 1, Example 2, and Comparative Example 2 may be summarized as follows. In Example 1, glucose concentration can be measured on the basis of output current values of the first enzyme electrode 2 in FIG. 1. Even with samples containing glucose of 30 mM, it is possible to measure sucrose concentration from output current values of the first and second enzyme electrodes 2, 4 as shown in FIG. 7. In Example 2, glucose concentration can be measured from output current value of the first enzyme electrode 2 in FIG. 9, and if samples contain glucose of 30 mM, it is possible to measure maltose concentration from output current values of the first and second enzyme electrodes as shown in FIG. 11. In contrast, it is apparent that in Comparative Examples 1 and 2, if samples contain glucose of 30 mM, the upper limit of the linear measurable range of the second enzyme electrode is already reached, it being unable to perform accurate measurement of sucrose (in Comparative Example 1) and maltose (in Comparative Example 2).

EXAMPLE 3

For the first enzyme electrode 2 in FIG. 1, a glucose detecting electrode having glucose oxidase immobilized thereon was employed, and for the second enzyme electrode 4 in FIG. 1, a glucose and lactose detecting electrode having glucose oxidase and β- galactosidase (Aspergillus oryzae, produced by Sigma) immobilized thereon was employed.

The construction of the first enzyme electrode 2 was the same as that in Example 1, and the second enzyme electrode 4 was prepared in the same manner as the second electrode 4 in Example 1. Other aspects of arrangement were the same as those in Example 1.

Figure 13:
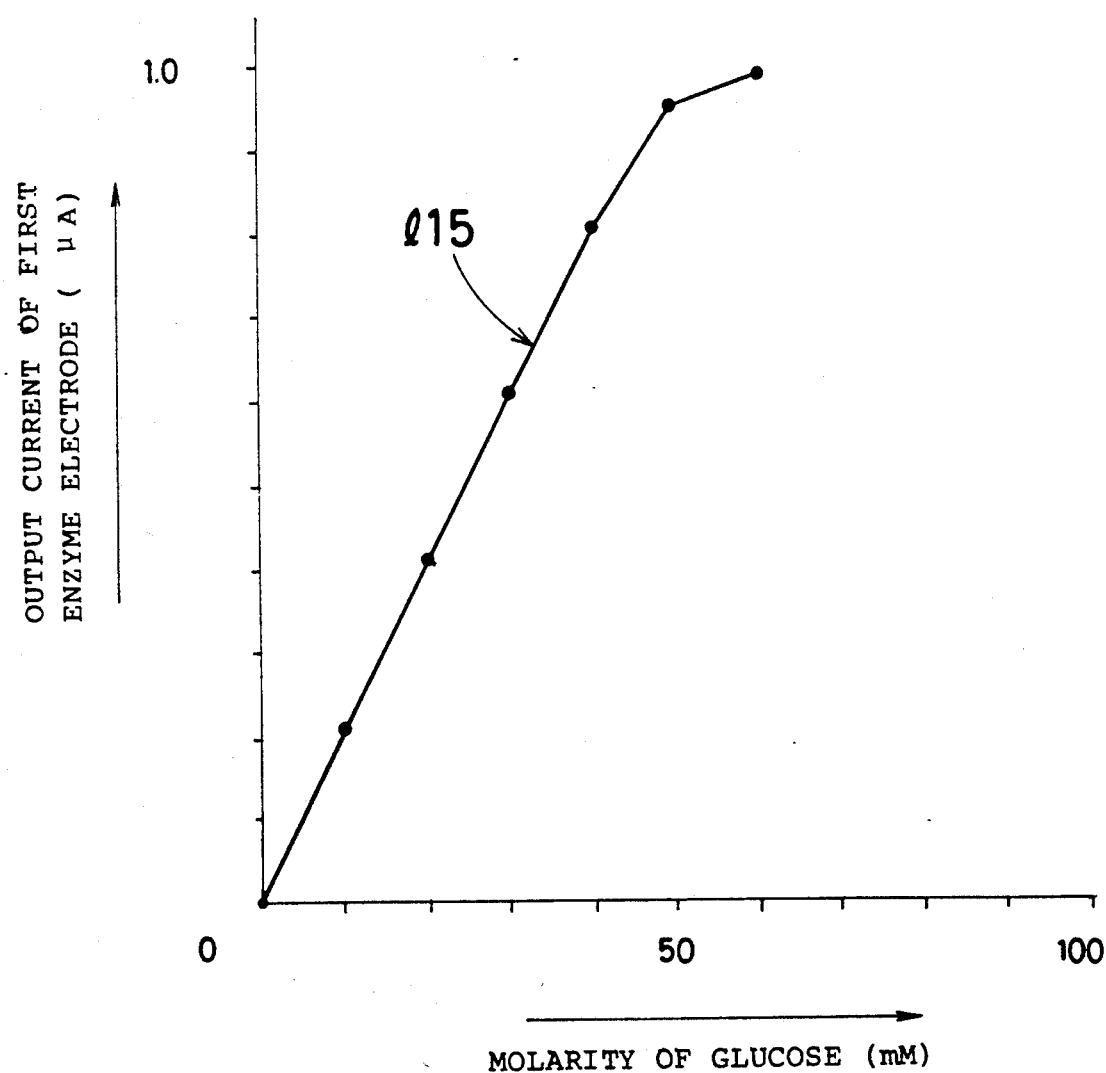
FIG. 13 is a graph showing the output current values of the first enzyme electrode 2 in response to glucose in Example 3.
Figure 14:
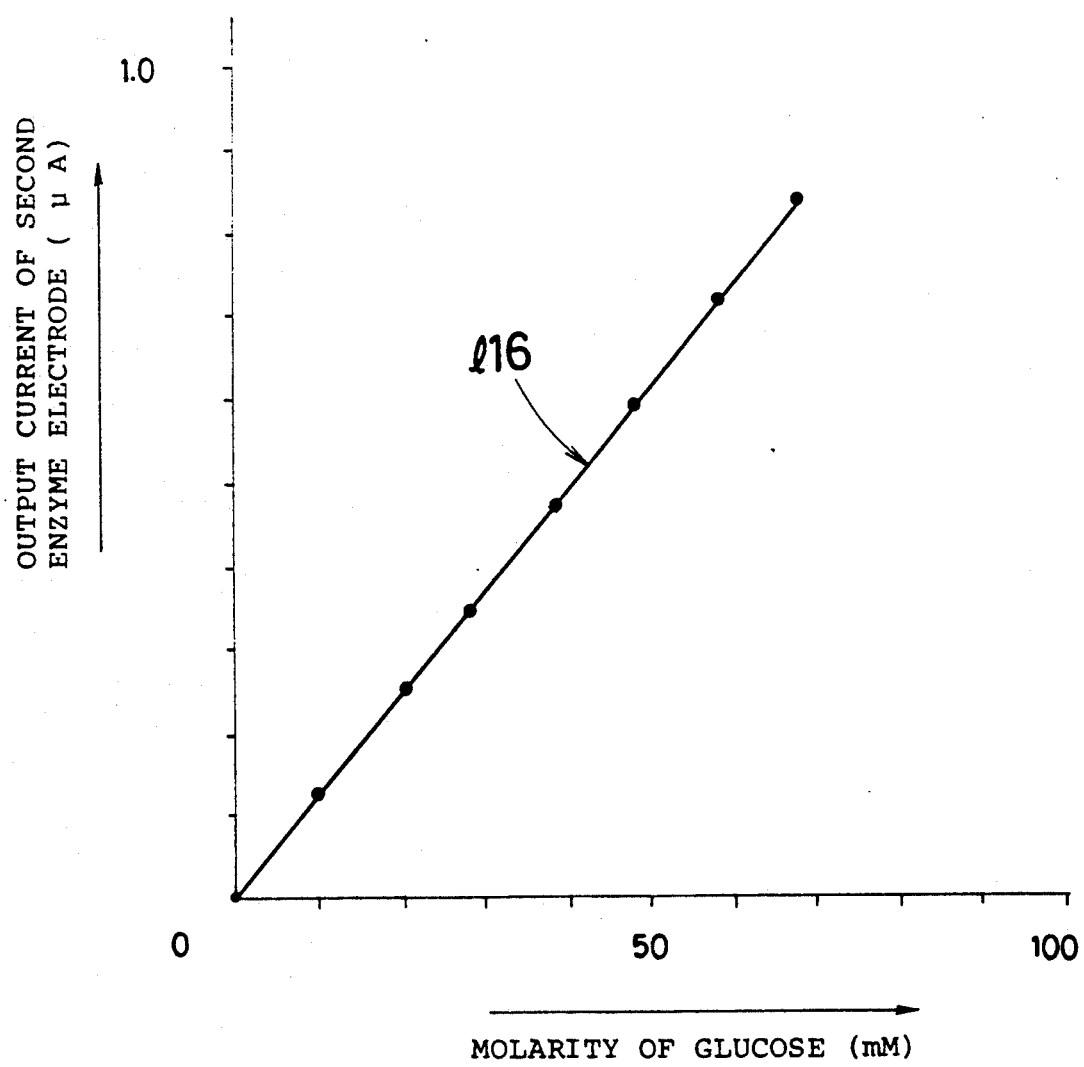
FIG. 14 is a graph showing the output current values of the second enzyme electrode 4 in response to glucose in Example 3.

In this system, 5 μl of an aqueous solution of glucose only (with a concentration range of 5-60 mM) was first injected through the injector 1, and a calibration curve as shown by line 115 in FIG. 13 was obtained from the first enzyme electrode 2. An aqueous solution of glucose only (with a concentration range of 5-70 mM) was injected in the amount of 5 μl through the injector 1, and a calibration curve as shown by line 16 in FIG. 14 was obtained from the second enzyme electrode 4 by virtue of the function of the dilution pipeline 5, the output of the second electrode 4 remained unsaturated.

Figure 15:
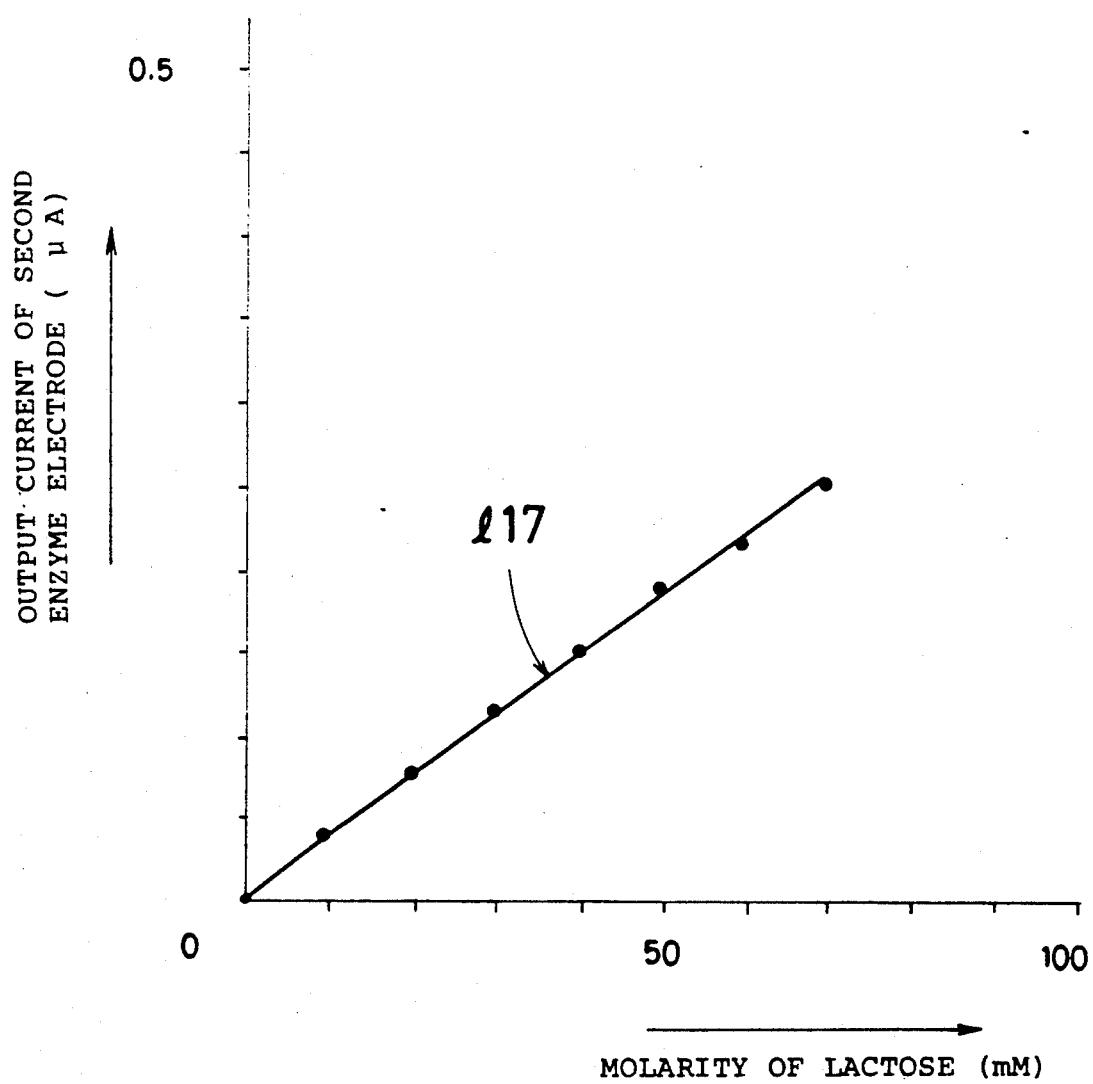
FIG. 15 is a graph showing a calibration curve of lactose in Example 3.

An aqueous solution of lactose only (with a concentration range of 0-70 mM) was injected in the amount of 5 μl through the injector 1, and a calibration curve shown by line 117 in FIG. 15 was obtained from the second enzyme electrode 4.

COMPARATIVE EXAMPLE 3

Figure 16:
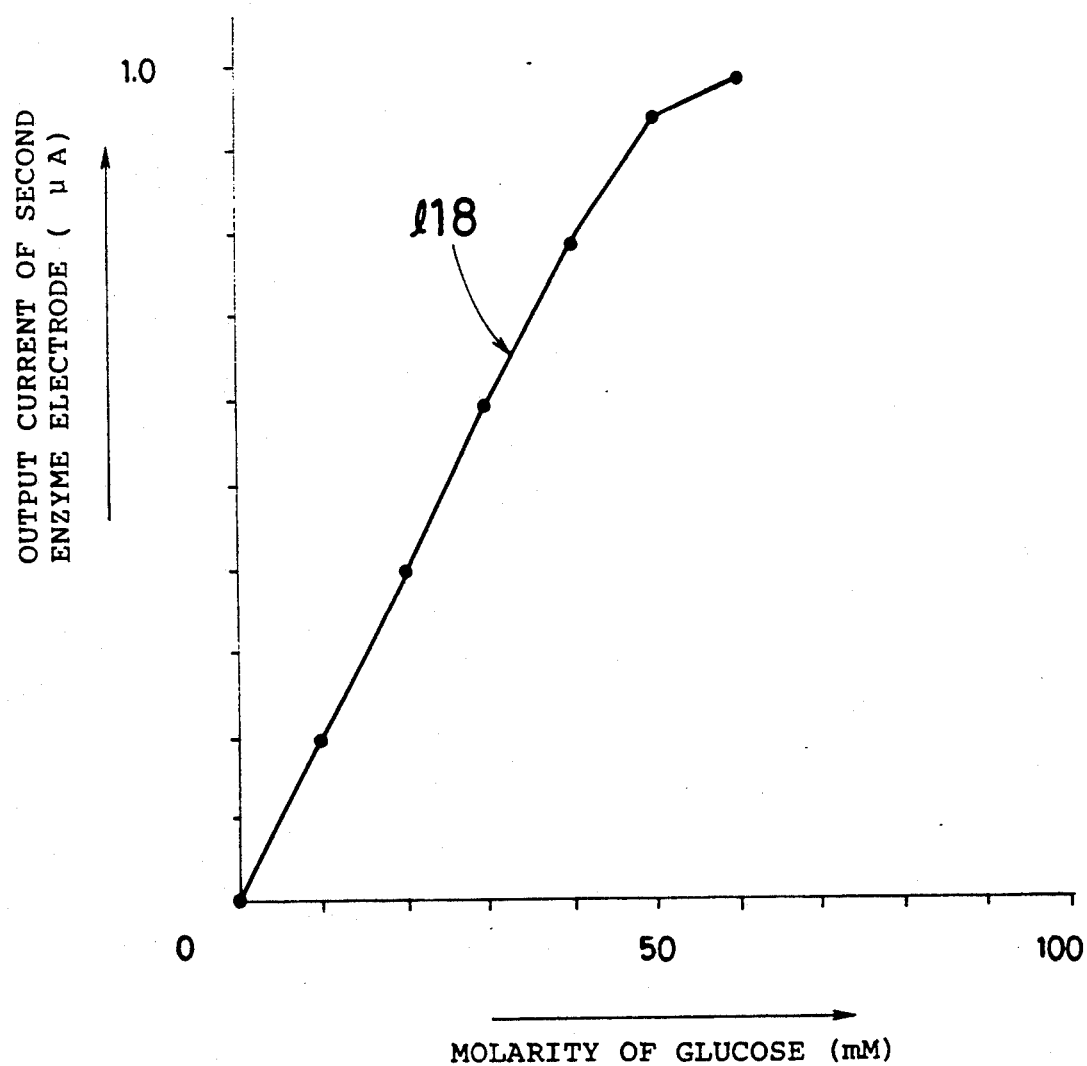
FIG. 16 is a graph showing the output current values of the second enzyme electrode in response to glucose without using the dilution pipeline 5 in Comparative Example 3.

Without using the dilution pipeline 5 in FIG. 1, the first and second enzyme electrodes 2, 4 were respectively mounted in the measuring cells 3, 11, and measurement was made in the same manner as in Example 3. It was confirmed that as line 118 in FIG. 16 shows, the calibration curve of the second enzyme electrode 4 became saturated at 50 mM. Therefore, where samples contained glucose of 50 mM and lactose, the output of the second enzyme electrode 4 deviated from the measurable proportional range thereof, and hence it was found impossible to perform accurate measurement of lactose concentration.

Example 3 and Comparative Example 3 may be summarized as follows. In Example 3, glucose concentration can be measured on the basis of output current values of the first enzyme electrode 2 as shown in FIG. 13. It is also apparent from FIGS. 14 and 15 that with samples containing glucose of 50 mM, lactose concentration can be measured from output current values of the first and second enzyme electrodes 2, 4. In contrast, it is confirmed that in Comparative Example 3, if samples contain glucose of 50 mM, the upper limit of the proportional measurable range of the second enzyme electrode 4 is already reached as shown in FIG. 16, it being thus impossible to perform accurate measurement of lactose.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A measuring apparatus having enzyme electrodes comprising:
    means for supplying a flow of buffer solution continuously at a constant flow rate,
    means for injecting a sample containing at least one of a first substance to be measured and a second substance to be measured into the flow of the buffer solution,
    a first measuring cell situated downstream of the injecting means, having a first flow path connected to the means for supplying, the capacity of the first flow path in the first measuring cell being about 5-100 μl,
    the first measuring cell equipped with a first enzyme electrode, the first enzyme electrode disposed to face the first flow path,
    the first enzyme electrode detecting the first substance, said first electrode containing an enzyme for catalyzing a reaction utilizing said first substance;
    a dilution pipeline situated downstream of the first measuring cell and for diluting the sample along the direction of the flow, having a flow path of an inner diameter of about 0.1-2.0 mm and an axial length of about 20-1000 cm, and
    a second measuring cell situated downstream of the dilution pipeline, having a second flow path connected to the dilution pipeline, the capacity of the second flow path in the second measuring cell being about 5-100 μl,
    the second measuring cell equipped with a second enzyme electrode disposed to face the second flow path, and said second electrode containing an enzyme for catalyzing a reaction utilizing said first substance and an enzyme for catalyzing a reaction to convert said second substance to said first substance, and for detecting (a) the first substance originally contained in the sample and (b) the first substance converted from the second substance,
    said first electrode, said dilution pipeline, and said second electrode forming a flow path for said buffer solution.

2. A measuring apparatus having enzyme electrodes comprising:
    means for supplying a flow of buffer solution continuously at a constant flow rate,
    means for injecting a sample containing at least one of a first substance to be measured and a second substance to be measured into the flow of the buffer solution,
    a first measuring cell situated downstream of the injecting means, having a first flow path connected to the means for supplying, the capacity of the first flow path in the first measuring cell being about 5-100 μl, the first measuring cell equipped with a first enzyme electrode and a first reference electrode, the first enzyme electrode disposed to face the first flow path, and having an immobilized enzyme of glucose oxidase, the first reference electrode in opposed relation to said first enzyme electrode and facing the first flow path, a dilution pipeline situated downstream of the first measuring cell, having a flow path of an inner diameter of about 0.1-2.0 mm and an axial length of about 20-1000 cm, and for diluting the sample along the direction of the flow, a second measuring cell situated downstream of the dilution pipeline, having a second flow path connected to the dilution pipeline, the capacity of the second flow path in the second measuring cell being about 5-100 μl, the second measuring cell equipped with a second enzyme electrode and a second reference electrode, the second enzyme electrode disposed to face the second flow path, and having immobilized enzymes of glucose oxidase, mutarotase and invertase, and the second reference electrode in opposed relation to said second enzyme electrode and facing the second flow path, said first measuring cell, said dilution pipeline, and said second measuring cell forming a flow path for said buffer solution.

3. A measuring apparatus having enzyme electrodes comprising:

means for supplying a flow of buffer solution continuously at a constant flow rate, means for injecting a sample containing at least one of a first substance to be measured and a second substrate to be measured into the flow of the buffer solution, a first measuring cell situated downstream of respect to the injecting means, having a first flow path connected to the means for supplying, the capacity of the first flow path in the first measuring cell being about 5-100 μl, the first measuring cell equipped with a first enzyme electrode and a first reflected electrode, the first enzyme electrode disposed to face the first flow path, and having an immobilized enzyme of glucose oxidase, the first reference electrode in opposed relation to said first enzyme electrode and facing the first flow path, a dilution pipeline situated downstream of the first measuring cell, having a flow path of an inner diameter of about 0.1-2.0 mm and an axial length of about 20-1000 cm, and for diluting the sample along the direction of the flow, a second measuring cell situated downstream of the dilution pipeline, having a second flow path connected to the dilution pipeline, the capacity of the second flow path in the second measuring cell being about 5-100 μl, the second measuring cell equipped with a second enzyme electrode and a second reference electrode, the second enzyme electrode disposed to face the second flow path, and having immobilized enzymes of glucose oxidase, mutarotase and α-glucosidase, and the second reference electrode in opposed relation to said second enzyme electrode and facing the second flow path, said first said first measuring cell, said dilution pipeline, and said second measuring cell forming a flow path for said buffer solution.

4. A measuring apparatus having enzyme electrodes comprising:

means for supplying a flow of buffer solution continuously at a constant flow rate, means for injecting a sample containing at least one of a first substance to be measured and a second substrate to be measured into the flow of the buffer solution, a first measuring cell situated downstream of the injecting means, having a first flow path connected to the means for supplying, the capacity of the first flow path in the first measuring cell being about 5-100 μl, the first measuring cell equipped with a first enzyme electrode and a first reflected electrode, the first enzyme electrode disposed to face the first flow path, and having an immobilized enzyme of glucose oxidase, the first reference electrode in opposed relation to said first enzyme electrode and facing the first flow path, a dilution pipeline situated downstream of the first measuring cell, having a flow path of an inner diameter of about 0.1-2.0 mm and an axial length of about 20-1000 cm, and for diluting the sample along the direction of the flow, a second measuring cell situated downstream of the dilution pipeline, having a second flow path connected to the dilution pipeline, the capacity of the second flow path in the second measuring cell being about 5-100 μl, the second measuring cell equipped with a second enzyme electrode and a second reference electrode, the second enzyme electrode disposed to face the second flow path, and having immobilized enzymes of glucose oxidase and β-glucosidase, and the second reference electrode in opposed relation to said second enzyme electrode and facing the second flow path, said first said first measuring cell, said dilution pipeline, and said second measuring cell forming a flow path for said buffer solution.

5. A measuring apparatus having enzyme electrodes comprising:

means for supplying a flow of buffer solution continuously at a constant flow rate, means for injecting a sample containing at least one of a first substance to be measured and a second substrate to be measured into the flow of the buffer solution, a first measuring cell situated downstream of the injecting means, having a first flow path connected to the means for supplying, the capacity of the first flow path in the first measuring cell being about 5-100 μl, the first measuring cell equipped with a first enzyme electrode and a first reflected electrode, the first enzyme electrode disposed to face the first flow path, and having an immobilized enzyme of glucose oxidase, the first reference electrode in opposed relation to said first enzyme electrode and facing the first flow path, a dilution pipeline situated downstream of the first measuring cell, having a flow path of an inner diameter of about 0.1-2.0 mm and an axial length of about 20-1000 cm, and for diluting the sample along the direction of the flow, and a second measuring cell situated downstream of the dilution pipeline, having a second flow path connected to the dilution pipeline, the capacity of the second flow path in the second measuring cell being about 5-100 µl, the second measuring cell equipped with a second enzyme electrode and a second reference electrode, the second enzyme electrode disposed to face the second flow path, and having immobilized enzymes of glucose oxidase and glucoamylase, and the second reference electrode in opposed relation to said second enzyme electrode and facing the second flow path, said first said first measuring cell, said dilution pipeline, and said second measuring cell forming a flow path for said buffer solution.

6. A measuring apparatus having enzyme electrodes comprising:

means for supplying a flow of buffer solution continuously at a constant flow rate, means for injecting a sample containing at least one of a first substance to be measured and a second substrate to be measured into the flow of the buffer solution, a first measuring cell situated downstream of the injecting means, having a first flow path connected to the means for supplying, the capacity of the first flow path in the first measuring cell being about 5-100 µl, the first measuring cell equipped with a first enzyme electrode and a first reflected electrode, the first enzyme electrode disposed to face the first flow path, and having an immobilized enzyme of glucose oxidase, the first reference electrode in opposed relation to said first enzyme electrode and facing the first flow path, a dilution pipeline situated downstream of the first measuring cell, having a flow path of an inner diameter of about 0.1-2.0 mm and an axial length of about 20-1000 cm, and for diluting the sample along the direction of the flow, a second measuring cell situated downstream of the dilution pipeline, having a second flow path connected to the dilution pipeline, the capacity of the second flow path in the second measuring cell being about 5-100 µl, the second measuring cell equipped with a second enzyme electrode and a second reference electrode, the second enzyme electrode disposed to face the second flow path, and having immobilized enzymes of glucose oxidase and lactase, and the second reference electrode in opposed relation to said second enzyme electrode and facing the second flow path, said first said first measuring cell, said dilution pipeline, and said second measuring cell forming a flow path for said buffer solution.

7. A measuring apparatus having enzyme electrodes comprising:

means for supplying a flow of buffer solution continuously at a constant flow rate, means for injecting a sample containing at least one of a first substance to be measured and a second substrate to be measured into the flow of the buffer solution, a first measuring cell situated downstream of the injecting means, having a first flow path connected to the means for supplying, the capacity of the first flow path in the first measuring cell being about 5-100 µl, the first measuring cell equipped with a first enzyme electrode and a first reflected electrode, the first enzyme electrode disposed to face the first flow path, and having an immobilized enzyme of cholesterol oxidase, the first reference electrode in opposed relation to said first enzyme electrode and facing the first flow path, a dilution pipeline situated downstream of the first measuring cell, having a flow path of an inner diameter of about 0.1-2.0 mm and an axial length of about 20-1000 cm, and for diluting the sample along the direction of the flow, a second measuring cell situated downstream of the dilution pipeline, having a second flow path connected to the dilution pipeline, the capacity of the second flow path in the second measuring cell being about 5-100 µl, the second measuring cell equipped with a second enzyme electrode and a second reference electrode, the second enzyme electrode disposed to face the second flow path, and having immobilized enzymes of cholesterol oxidase and cholesterol esterase, and the second reference electrode in opposed relation to said second enzyme electrode and facing the second flow path, said first said first measuring cell, said dilution pipeline, and said second measuring cell forming a flow path for said buffer solution.

8. The measuring apparatus claimed in any one of claims 1 to 7, wherein the flow path of the dilution pipeline has an axial length of about 50-300 cm.

9. The measuring apparatus claimed in any one of claims 1 to 7, wherein the first or second enzyme electrode has a membrane of selective permeability on a conductive electrode.

10. The measuring apparatus claimed in any one of claims 1 to 7, wherein the first or second enzyme electrode has a membrane of selective permeability and an immobilized enzyme layer on a conductive electrode.

11. The measuring apparatus claimed in claim 1, wherein the first measuring cell is equipped with a first reference electrode, the first reference electrode being in opposed relation to the first enzyme electrode, which faces the first flow path.

12. The measuring apparatus claimed in claim 1, wherein the second measuring cell is equipped with a second reference electrode, the second reference electrode being in opposed relation against the second enzyme electrode, which faces the second flow path.

13. The measuring apparatus claimed in claim 1, wherein second measuring cell being equipped with a second reference electrode, the dilution pipeline being coiled.

14. A method of measuring the amount in a sample of at least one substance which is capable of undergoing enzyme-catalyzed reaction, which method comprises:

i) providing a measuring apparatus which comprises
(a) a first enzyme electrode for detecting a first substance to be measured, said electrode containing an enzyme for catalyzing a reaction utilizing said first substance, (b) a dilution pipeline situated downstream of respect to the first enzyme electrode, and (c) a second enzyme electrode situated downstream of respect to the dilution pipeline, containing an enzyme for catalyzing a reaction for converting a second substance to be measured into the first substance, and an enzyme for catalyzing a reaction utilizing the first substance, said first electrode, said dilution pipeline and said second electrode forming a flow path for a buffer solution, said method comprising the steps of:

ii) supplying a constant flow of said buffer solution to said first electrode, said buffer solution traveling along said flow path and being discharged from said second electrode, iii) injecting the first substance into the flow of the buffer solution upstream with respect to the first enzyme electrode, (iv) measuring an output current value at said first and second enzyme electrode, v) calculating a response ratio k1, which is represented by the following equation (1), $$K1 = ib/ia \quad (1)$$

wherein the output current value of the first enzyme electrode is represented by ia and output current value of the second enzyme electrode is represented by ib, vi) injecting a sample to be analyzed containing at least one of the first substance and the second substance into the flow of the buffer solution upstream with respect to the first enzyme electrode, and vii) measuring an output current value at said first and second enzyme electrode, and viii) calculating a value i3 which is proportionate to the concentration of the second substance in said sample, said value being represented by the following equation (2), $$i3 = i2 - k1 \cdot i1 \quad (2)$$

wherein the output current value of the first enzyme electrode is represented by i1 which is proportionate to the concentration of the first substance in said sample, and output current value of the second enzyme electrode is represented by i2.

15. The method according to claim 14 wherein said dilution pipeline has an inner diameter of about 0.1 to 2.0 mm and an axial length of about 20–1000 cm, wherein the capacity of said flow path associated with said first electrode is about 5–100 $\mu$l and wherein the capacity of the flow path associated with said second electrode is about 5–100 $\mu$l.

* * * * *